United States Patent [19]

Hermecz et al.

[11] Patent Number: 5,252,572
[45] Date of Patent: Oct. 12, 1993

[54] PYRIDOPYRIMIDINE DERIVATIVES, PHARMACEUTICAL COMPOSITIONS CONTAINING THEM AND PROCESS FOR PREPARING SAME

[75] Inventors: István Hermecz; József Knoll; Lelle Vasvári, née Debreczy; Klára Gyires; Judit Sipos; Ágnes Horváth; László Tardos, all of Budapest; Mária Blaogh, Dunakeszi, all of Hungary

[73] Assignee: Chinoin Gyogyszer- Es Vegyeszeti Termekek Gyara Rt., Budapest, Hungary

[21] Appl. No.: 903,246

[22] Filed: Jun. 23, 1992

Related U.S. Application Data

[63] Continuation of Ser. No. 307,665, Feb. 6, 1989, Pat. No. 5,158,951.

[51] Int. Cl.$^5$ .................. A61K 31/505; C07D 471/04
[52] U.S. Cl. ..................................... 514/258; 544/282
[58] Field of Search ........................ 544/282; 514/258

[56] References Cited

U.S. PATENT DOCUMENTS

| | | | |
|---|---|---|---|
| 4,209,622 | 6/1980 | Meszaros et al. | 544/282 |
| 4,252,807 | 2/1981 | Hermecz et al. | 424/251 |
| 4,260,612 | 4/1981 | Hermecz et al. | 424/251 |
| 4,291,036 | 9/1981 | Knoll et al. | 424/251 |
| 4,452,982 | 6/1984 | Hermecz et al. | 544/282 |
| 4,460,771 | 7/1984 | Meszaros et al. | 544/282 |
| 4,472,398 | 9/1984 | Meszaros et al. | 424/251 |
| 4,495,189 | 1/1985 | Meszaros et al. | 514/258 |

OTHER PUBLICATIONS

Magyar Kemikusol Papja 31, pp. 281–292 (1976) and Partial English Translation.

*Primary Examiner*—Thurman K. Page
*Assistant Examiner*—Jyothsna Venkat
*Attorney, Agent, or Firm*—Herbert Dubno; Jonathan Myers

[57] ABSTRACT

The present invention relates to novel 4-oxo-4H-pyrido[1,2-a]pyrimidine-3-carboxamide derivatives of the general formula (I) and the acid addition salts thereof, pharmaceutical compositions containing them and a process for their preparation. In the general formula (I)

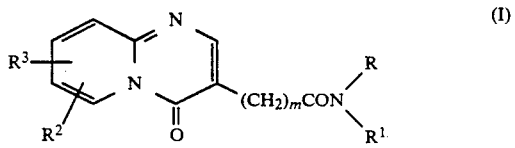

R stands for a $C_{1-12}$alkyl group optionally substituted by a $C_{1-4}$ alkoxycarbonyl group; a $C_{3-9}$cycloalkyl, adamantyl or optionally substituted phenyl group;

$R^1$ means hydrogen or a $C_{1-4}$alkyl group; or

R and $R^1$ together form a —$(CH_2)_n$— chain, wherein n is 4, 5 or 6;

$R^2$ stands for hydrogen, a $C_{1-4}$alkyl group or halogen;

$R^3$ represents hydrogen or a $C_{1-4}$alkyl group; and m is 0 or 1.

The compounds of the general formula (I) possess a gastroprotective effect and are useful for the prevention and therapy of ulcers of the stomach and the small intestine.

7 Claims, No Drawings

PYRIDOPYRIMIDINE DERIVATIVES, PHARMACEUTICAL COMPOSITIONS CONTAINING THEM AND PROCESS FOR PREPARING SAME

This is a continuation of co-pending application Ser. No. 07/307,665 filed on 6 Feb. 1989, now U.S. Pat. No. 5,158,951.

FIELD OF THE INVENTION

This invention relates to novel 4-oxo-4H-pyrido[1,2-a]pyrimidine-3-carboxamide derivatives and their acid addition salts which are useful as gastroprotective agents mainly for the therapy and prevention of ulcer.

BACKGROUND OF THE INVENTION

It is known that 4-oxo-4H-pyrido[1,2-a]pyrimidine derivatives have analgesic and other effects influencing the central nervous system (British Patent No. 1,209,946, U.S. Pat. No. 4,291,036 and German Patent No. 2,414,751). One of the most advantageous representatives of these compounds is 1,6-dimethyl-3-ethoxycarbonyl-6-methyl-4-oxo-4H-pyrido[1,2-a]-pyrimidinium methosulfate [Arzneimittelforschung 22, 815 (1972)] used as an analgesic drug in clinical practice. Other derivatives have been shown to exert a preferable anti-arteriosclerotic (German Patent No. 2,705,775), antiallergic and antiasthmatic (Belgian Patent Nos. 873,192 and 873,194), anti-inflammatory [German Patent Nos. 2,728,198 and 2,526,983; Arzneimittelforschung 29, 766 (1979)], cardiovascular [Sankyo Kenkyusho Nempo 29, 75 (1977)] and selective serotonine-2 receptor-blocking (U.S. Pat. No. 4,342,870) effects. The antiulcer action of tetrahydro- and hexahydro-4-oxo-4H-pyrido[1,2-a]-pyrimidine-3-carboxylic acid derivatives have also been reported [Drugs Exptl. Clin. Res. 11, 493 (1985); ibidem 13, 253 (1987)]. Some unsaturated 4-oxo-4H-pyrido[1,2-a]pyrimidine-3-carboxylic acid derivatives showed an analgesic action which, however, could not be utilized because of the hydrolytic instability of the bicyclic moiety [Magyar Kdmikusok Lapja 31, 281 (1976)].

DESCRIPTION OF THE INVENTION

The invention relates to novel 4-oxo-4H-pyrido[1,2-a]pyrimidine-3-carboxamide derivatives of the formula (I),

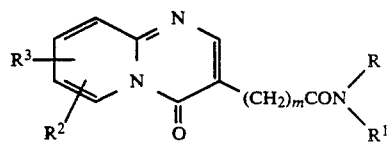

wherein
R stands for a $C_{1-12}$alkyl group optionally substituted by a $C_{1-4}$ alkoxycarbonyl group; a $C_{3-9}$cycloalkyl, adamantyl or optionally substituted phenyl group;
$R^1$ means hydrogen or a $C_{1-4}$alkyl group; or
R and $R^1$ together form a —$(CH_2)_n$— chain, wherein n is 4, 5 or 6;
$R^2$ stands for hydrogen, a $C_{1-4}$alkyl group or halogen;
$R^3$ represents hydrogen or a $C_{1-4}$alkyl group; and
m is 0 or 1 as well as their pharmaceutically acceptable acid addition salts and pharmaceutical preparations containing these compounds.

As used herein: the term "$C_{1-4}$alkyl" or "$C_{1-4}$alkyl" means straight or branched chain aliphatic saturated hydrocarbyl groups such as the methyl, ethyl, n-propyl, isopropyl, n-butyl, isobutyl, sec.-butyl, tert.-butyl and neopentyl group; the term "$C_{3-9}$cycloalkyl" means a saturated alicyclic hydrocarbyl group optionally bearing an alkyl group such as the cyclopropyl, methylcyclopropyl, cyclobutyl, 2,3-dimethylcyclobutyl or cyclohexyl group; the term "optionally substituted phenyl" means a phenyl group, or a phenyl group mono- or polysubstituted by halogen, $C_{1-4}$alkyl, $C_{2-5}$alkoxy, hydroxyl, trifluoromethyl, cyano, $C_{1-4}$alkoxycarbonyl or carboxyl group or substituted by a methylenedioxy group; the term "halogen" means fluorine, chlorine, bromine or iodine atom.

The compounds of the formula (I) can form acid addition salts with pharmaceutically acceptable organic and inorganic acids (e.g. hydrochlorides, hydrobromides, hydroiodides, sulfates, nitrates, perchlorates and phosphates; as well as mesylates, maleates, succinates, acetates, tartrates, lactates, fumarates and citrates).

According to another aspect of the invention, there is provided a process for the preparation of the new compounds of the formula (I), wherein R, $R^1$, $R^2$, $R^3$ and m are the same as defined above, and their pharmaceutically acceptable acid addition salts, which comprises a) reacting a 4-oxo-4H-pyrido[1,2-a]pyrimidine-3-carboxylic acid ester of the formula (II),

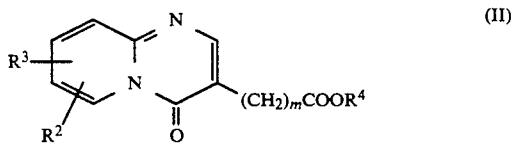

wherein $R^2$, $R^3$ and m are the same as defined above and $R^4$ stands for a $C_{1-4}$alkyl group, with an amine of the formula (III),

wherein R and $R^1$ are the same as defined above; or b) reacting a 4-oxo-4H-pyrido[1,2-a]pyrimidine-3-carboxylic acid mixed anhydride of the formula (IV),

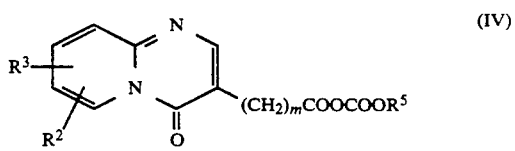

wherein $R^2$, $R^3$ and m are the same as defined above and $R^5$ means a $C_{1-4}$alkyl or a benzyl group, with an amine of the formula (III), wherein R and $R^1$ are the same as defined above, and, if desired, converting the thus obtained compound of the general formula (I), wherein R, $R^1$, $R^2$, $R^3$ and m are the same as defined above, with a pharmaceutically acceptable acid to the corresponding salt thereof or, if desired, liberating it from its salt or, if desired, liberating it from one of its salts and converting it to another salt thereof in a known way.

The process a) according to the invention is preferably carried out in the presence of a solvent. Organic solvents commonly employed in amidation reactions may be used. The reaction temperature may be chosen according to the properties of the reactant. The reaction may be accomplished at room temperature or at the boiling point of the solvent, However, another temperature may be used. If desired, the reaction may be carried out at a pressure different from atmospheric, preferably under an overpressure. When a water-miscible organic solvent, e.g. alcohol is used, the reaction mixture may contain an optional amount of water. In a number of cases, the compound of the formula (I) obtained is precipitated from the reaction mixture after dilution with water and may be recovered by filtration. Alternatively it may be isolated by recrystallization of the residue after evaporation of the solvent.

In the process b) according to the invention, the compound of the formula (IV), wherein $R^2$, $R^3$ and m are the same as defined above and $R^5$ means a $C_{1-4}$alkyl or benzyl group, is prepared in situ by using as a starting material the carboxylic acid of the formula (V),

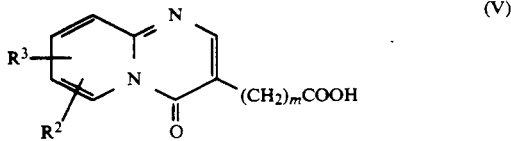

wherein $R^2$ and $R^3$ are the same as defined above, and the chloroformate ester of the formula (VI),

Cl—COOR$^5$ (VI)

wherein $R^5$ is the same as defined above, in a manner known per se.

According to an embodiment of the process b), a compound of the formula (V) is dissolved in an organic solvent, preferably in a chlorinated hydrocarbon (most preferably in chloroform) or in an ether, (most preferably in dioxane or tetrahydrofuran) and, after adding a trialkylamine, preferably triethylamine or tributylamine, a compound of the formula (VI), preferably methyl, ethyl, benzyl or isopropyl chloroformate is dropwise added to the solution obtained at a temperature between −30° C. and 50° C., preferably between −20° C. and 0° C. To the compound of the formula (IV) thus obtained, wherein $R^5$ is the same as defined above, an amine of the general formula (III) is added dropwise (if desired, as a solution) in the solvent defined above or, on the use of its acid addition salt, together with a trialkylamine, preferably with triethylamine or tributylamine), and the reaction mixture is stirred at the temperature range defined above and then allowed to warm to room temperature and subsequently washed with an aqueous sodium hydrogen carbonate solution and then with water. After drying, the reaction mixture is evaporated and the residue is recrystallized from a suitable solvent.

The ratio of the reactants may arbitrarily be selected in both processes a) and b). It is preferable to react 1 mole of a compound of the formula (II) or (IV), wherein $R^2$, $R^3$, $R^4$ and $R^5$ are the same as defined above, with 1 to 10 moles of the amine of the formula (III), wherein R and $R^1$ are the same as defined above.

A part of the compounds containing a bridgehead nitrogen used as starting materials are known. The starting substances of the formulae (II) and (V) are known from the literature [Arnzeimittelforschung 22, 815 (1972)] or may be prepared in an analogous manner. The amines of the formula (III) and compounds of the formula (VI) are commercially available.

The toxicity of the compounds of the formulae (I) and (II) is low, in general their oral $L_{50}$ values are higher than 250 mg/kg in rats and mice.

The compounds of the formula (I) and their pharmaceutically acceptable salts possess a significant gastroprotective effect and exert their protective and healing (therapeutic) action both in the stomach and the small intestine as well. The activity of the compounds of the formula (I) was demonstrated in standard tests generally accepted for determining the antiulcerogenic effect.

As an example, the efficacy on the gastric ulcer induced in rats by 0.5 ml of a mixture containing 96% ethanol and hydrochloric acid in an 1:0.02 volume ratio is illustrated in Table 1 [for the method, see: Gastroenterology 77, 433 (1979)].

TABLE 1

Protective action in rats of the compounds according to the invention against the gastric mucosa laesion induced by 96% ethanol containing hydrochloric acid

| Compound | Oral dose mg/kg | Inhibition of the gastric ulcer % |
|---|---|---|
| N-tert.-pentyl-6-methyl-4-oxo-4H-pyrido[1,2-a]-pyrimidine-3-carboxamide | 50 | 77 |
| N-isopropyl-6-methyl-4-oxo-4H-pyrido[1,2-a]pyrimidine-3-carboxamide | 50 | 95 |
| N-neopentyl-6-methyl-4-oxo-4H-pyrido[1,2-a]pyrimidine-3-carboxamide | 100 | 48 |
| 6-methyl-4-oxo-3-pyrrolidino-carbonyl-4H-pyrido[1,2-a]-pyrimidine | 50 | 53 |
| N,6-dimethyl-4-oxo-4H-pyrido-[1,2-a]pyrimidine-3-carboxamide | 100 | 48 |
| N-propyl-6-methyl-4-oxo-4H-pyrido[1,2-a]pyrimidine-3-carboxamide | 12.5 | 69 |

The effect of the compounds according to the invention, given as examples, against the indomethacin-induced ulcer [Arch. Int. Pharmacodyn. 117, 113 (1964)] is shown in Table 2.

TABLE 2

Inhibition of the indomethacin-induced gastric mucosa laesion in rats

| Compound | Oral dose mg/kg | Inhibition of the gastric ulcer % |
|---|---|---|
| 6-methyl-4-oxo-3-pyrrolidino-carbonyl-4H-pyrido[1,2-a]-pyrimidine | 50 | 46 |
| N,6-dimethyl-4-oxo-4H-pyrido-[1,2-a]pyrimidine-3-carboxamide | 50 | 64 |
| N-tert.-octyl-6-methyl-4-oxo-4H-pyrido[1,2-a]pyrimidine-3-carboxamide | 50 | 15 |
| N-tert.-pentyl-6-methyl-4-oxo-4H-pyrido[1,2-a]pyrimidine-3-carboxamide | 100 | 38 |
| N-neopentyl-6-methyl-4-oxo-4H-pyrido[1,2-a]pyrimidine-3-carboxamide | 50 | 43 |
| N-isopropyl-6-methyl-4-oxo-4H-pyrido[1,2-a]pyrimidine-3-carboxamide | 100 | 88 |

TABLE 2-continued

Inhibition of the indomethacin-induced gastric mucosa laesion in rats

| Compound | Oral dose mg/kg | Inhibition of the gastric ulcer % |
|---|---|---|
| N-propyl-6-methyl-4-oxo-4H-pyrido[1,2-a]pyrimidine-3-carboxamide | 12.5 | 48 |

The inhibiting effect N-propyl-6-methyl-4-oxo-4H-pyrido[1,2-a]pyrimidine-3-carboxamide on the formation of the indomethacin-induced duodenal ulcer in rats is given as an example. This compound was administered in a dose of 50 mg/kg on 4 consecutive days. On the 2nd day, a 15 mg/kg oral dose of indomethacin was given to unstarved rats. The ulcer formation was determined in the small intestine by using the method of Tsuromi [J. Pharm. Dyn. 3, 659 (1980)] on the 3rd day following the administration of indomethacin. In comparison to the control, the compound according to the invention exerted an inhibition of 58% on the ulcer formation.

The compound of the formula (I) or its salts may therapeutically be used in the form of compositions containing the active ingredient in an admixture with inert solid or liquid organic or inorganic carriers. These compositions can be prepared by using methods well known in the pharmaceutical industry.

The compositions may be formulated for oral or parenteral use in the form of e.g. tablets, dragées, capsules or in the sustained-release variants thereof. The compositions may contain suitable solid diluents or carriers, sterile aqueous solvents or non-toxic organic solvents. The compositions for oral use may be supplemented with sweetening or flavoring (aromatizing) agents which are suitable for this purpose.

Tablets for oral use may contain: carriers such as lactose, sodium citrate, or calcium carbonate; disintegrating agents such as starch or alginic acid; and sliding agents such as talc, sodium lauryl sulfate or magnesium stearate. The carrier in capsules may be e.g. lactose or polyethylene glycol. Aqueous suspensions may contain emulsifying or suspending agents. The diluent of a suspension in an organic solvent may be glycerol, ethanol, chloroform and the like.

The compositions for parenteral use are solutions or suspensions of the active ingredient in a suitable medium such as peanut oil, sesame oil, polypropylene glycol or water.

The active ingredient content of the pharmaceutical compositions according to the invention may be varied within wide limits, say; 0.005 to 99%.

The daily dose of the active ingredient may also be varied within wide limits and depends on the severity of the disease as well as on the age and body weight of the patient, on the formulation of the composition and efficiency of the active ingredient used. For oral use, the daily dose of the active ingredient is commonly between 0.05 and 15 mg/kg daily once or in divided doses. However, the above data are only informative in character, which may be increased or lowered, dependently on the demands of the situation and prescriptions of the physician. When justified, compositions (formulations) differing from the above application forms may also be used.

SPECIFIC EXAMPLES

The invention is illustrated in detail by the following non-limiting Examples.

EXAMPLE 1

Preparation of N,6-dimethyl-4-oxo-4H-pyrido[1,2-a]pyrimidine-3-carboxamide

A solution containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below $-10°$ C. while stirring and cooling by ice-salt. To this mixture, 6.5 ml (0.08 mol) of methyl chloroformate dissolved in 40 ml chloroform are dropped at $-20°$ C. during 10 minutes. After stirring for 5 minutes, a solution containing 2.5 g (0.08 mol) of methylamide (prepared from methylamine hydrochloride in chloroform by adding triethylamine) in 80 ml of chloroform is added dropwise to the reaction mixture at $-18°$ C. during 30 minutes. After stirring below $-10°$ C. for 1 hour, the reaction mixture is allowed to stand in the refrigerator overnight. Next day the reaction mixture is washed 3 times with 140 ml of 5% sodium hydrogen carbonate solution each and then with 140 ml of water. The organic phase is dried over anhydrous sodium sulfate and evaporated under reduced pressure. The residue is stirred with 150 ml of 10% hydrochloric acid at room temperature for 1 hour, then the precipitated starting material, 6-methyl-4-oxo-4H-pyrido[1,2-a]pyrimidine-3-carboxylic acid weighing 10 g is filtered off. The pH value of the aqueous filtrate is adjusted to 9 by adding 20% sodium hydroxide solution and then extracted 3 times with 100 ml of chloroform each. The combined organic phase is dried over anhydrous sodium sulfate and evaporated. After recrystallization of the residue from ethanol, 3.2 g (45.5%) of the named lemon-yellow product are obtained, m.p.: $208°$–$210°$ C.

Analysis: Calculated for $C_{11}H_{11}N_3O_2$ C 60.82; H 5.10; N 19.34%; found C 60.91; H 5.18; N 19.31%.

EXAMPLE 2

Preparation of N-propyl-6-methyl-4-oxo-4H-pyrido[1,2-a]pyrimidine-3-carboxamide

A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below $-10°$ C. by ice-salt. A solution of 6.5 ml (0.08 mol) of methyl chloroformate in 40 ml of chloroform is added dropwise to the above mixture at $-10°$ C. during 20 minutes. After stirring for 5 minutes, a solution containing 5.2 g (0.088 mol) of propylamine in 80 ml of chloroform is added dropwise at $-15°$ C. during 30 minutes, then the mixture is stirred for 1 hour below $-10°$ C. Then the mixture is allowed to stand overnight under cooling by ice. For working up, the chloroform mixture is washed 3 times with 150 ml of 5% sodium hydrogen carbonate solution each and then 3 times with 150 ml of water each. The chloroform phase is dried over anhydrous sodium sulfate, filtered and evaporated to give 16.8 g (85.6%) of the named product in the form of yellow crystals after recrystallization from ethanol, m.p.: $158°$–$160°$ C.

Analysis: Calculated for $C_{13}H_{15}N_3O_2$ C 63.66; H 6.16; N 17.13%; found C 63.72; H 6.24; N 17.34%.

EXAMPLE 3

Preparation of
N-isopropyl-6-methyl-4-oxo-4H-pyrido[1,2-a]pyrimidine-3-carboxamide A mixture containing 16.32 g (0.08 mol) of 6-methyl-4-oxo-4H-pyrido[1,2-a]pyrimidine-3-carboxylic acid and 12.4 ml (0.088 mole) of triethylamine in 480 ml of chloroform is cooled below −10° C. by ice-salt. A solution of 6.5 ml (0.08 mol) of methyl chloroformate in 40 ml of chloroform is dropped to the above mixture at a temperature between −12° C. and −16° C. during 30 minutes. After stirring for 5 minutes, 5.2 g (0.088 mol) of isopropylamine dissolved in 80 ml of chloroform are dropped to the above solution at −15° C. during 40 minutes, then the mixture is stirred for 1 hour at the same temperature and thereafter maintained under cooling by ice.

For working up, the mixture is washed 3 times with 150 ml of 5% sodium hydrogen carbonate solution each and then 3 times with 150 ml of water each. After during over anhydrous sodium sulfate, the chloroform solution is filtered and evaporated to give 13.2 g (67.3%) of the named product as yellow crystals after recrystallization from ethanol, m.p.: 165°–169° C.

Analysis: Calculated for $C_{13}H_{15}N_3O_2$ C 63.66; H 6.16; N 17.13%; found C 63.57; H 6.09; N 17.18%.

EXAMPLE 4

Preparation of
N-butyl-4-oxo-4H-pyrido[1,2-a]pyrimidine-3-carboxamide

A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below −10° C. by ice-salt. A solution of 6.5 ml (0.08 mol) of methyl chloroformate in 40 ml of chloroform is dropped to the above mixture at a temperature between −12° C. and −15° C. during 15 minutes. After stirring for 5 minutes, 6.43 g (0.088 mol) of butylamine dissolved in 80 ml of chloroform are dropped to the above solution at a temperature between −10° C. and −15° C. during 50 minutes. The reaction mixture is stirred for 1 hour at the same temperature and then let to stand under cooling by ice. For working up, the mixture is washed 3 times with 150 ml of 5% sodium hydrogen carbonate solution each and then 3 times with 150 ml of water each. The organic phase is dried over anhydrous sodium sulfate and evaporated to give 14.9 g (71.8%) of the named product as yellow crystals, m.p.: 127°–130° C.

Analysis: Calculated for $C_{14}H_{17}N_3O_2$ C 64.85; H 6.61; N 16.20%; found C 64.78; H 6.54; N 16.27%.

EXAMPLE 5

Preparation of
N-tert.-butyl-6-methyl-4-oxo-4H-pyrido[1,2-a]pyrimidine-3-carboxamide A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below −10° C. by ice-salt. A solution of 6.5 ml (0.08 mol) of methyl chloroformate in 40 ml of chloroform is dropped to the above mixture at −20° C. during 20 minutes. After stirring for 5 minutes, 6.47 g (0.088 mol) of tert.-butylamine dissolved in 80 ml of chloroform are dropped to the above solution at a temperature between −18° C. and −20° C. during 50 minutes. The reaction mixture is stirred for 1 hour at the same temperature and then let to stand in the refrigerator overnight. For working up, the mixture is washed 3 times with 150 ml of 5% sodium hydrogen carbonate each and then 3 times with 150 ml of water each. The organic phase is dried over anhydrous sodium sulfate and evaporated to give 15.5 g (74.7%) of the named product as light beige crystals after recrystallization from ethanol, m.p.: 164°–166° C.

Analysis: Calculated for $C_{14}H_{17}N_3O_2$ C 64.85; H 6.61; N 16.20%; found C 64.91; H 6.75; N 16.23%.

EXAMPLE 6

Preparation of
N-pentyl-6-methyl-4-oxo-4H-pyrido[1,2-a]pyrimidine-3-carboxamide

A mixture containing 8.16 g (0.04 mol) of 6-methyl-4-oxo-4H-pyrido[1,2-a]pyrimidine-3-carboxylic acid and 6.2 ml (0.044 mol) of triethylamine in 240 ml of chloroform is cooled below −10° C. by ice-salt. A solution of 4 ml (0.042 mol) of ethyl chloroformate in 20 ml of chloroform is dropped to the above mixture at −15° C. during 20 minutes. After stirring for 5 minutes, 3.835 g (0.044 mol) of n-pentylamine dissolved in 40 ml of chloroform are dropped to the above solution at −15° C. during 20 minutes. The reaction mixture is stirred below −10° C. for 1 hour and then let to stand overnight under cooling by ice. For working up, the reaction mixture is washed 3 times with 100 ml of 5% sodium hydrogen carbonate solution each and then 3 times with 100 ml of water each. The organic phase is dried over anhydrous sodium sulfate, filtered and evaporated to give 6.1 g (55.8%) of the named product as orange yellow crystals after recrystallization from ethanol, m.p.: 112°–116° C.

Analysis: Calculated for $C_{15}H_{19}N_3O_2$ C 65.91; H 7.01; N 15.37%; found C 65.87; H 7.13; N 15.45%.

EXAMPLE 7

Preparation of N-neopentyl-6-methyl-4-oxo-4H-pyrido[1,2-a]pyrimidine-3-carboxamide A mixture containing 8.16 g (0.04 mole) of 6-methyl-4-oxo-4H-pyrido[1,2-a]pyrimidine-3-carboxylic acid and 6.2 ml (0.044 mol) of triethylamine in 240 ml of chloroform is cooled below −10° C. by ice-salt. A solution of 3.25 ml (0.04 mol) of methyl chloroformate in 20 ml of chloroform is dropped to the above solution at −16° C. during 10 minutes. After stirring for 5 minutes, 3.83 g (0.044 mol) of neopentylamine dissolved in 10 ml of chloroform are dropped to the above solution at −10° C. during 5 minutes. After stirring at −10° C. for 1 hour, the reaction mixture is washed 3 times with 80 ml of 5% sodium hydrogen carbonate solution each and then 3 times with 80 ml of water each. The organic phase is dried over anhydrous sodium sulfate and then evaporated to give 6.8 g (62.2%) of the named product as yellow crystals after recrystallization from ethanol, m.p.: 191°–194° C.

Analysis: Calculated for $C_{15}H_{19}N_3O_2$ C 65.91; H 7.01; N 15.37%; found C 65.89; H 6.95; N 15.39%.

EXAMPLE 8

Preparation of
N-hexyl-6-methyl-4-oxo-4H-pyrido[1,2-a]pyrimidine-3-carboxamide

A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below $-10°$ C. by ice-salt. A solution of 6.5 ml (0.08 mol) of methyl chloroformate in 40 ml of chloroform is dropped to the above mixture at a temperature between $-11°$ C. and $-12°$ C. during 20 minutes. After stirring for 5 minutes, 8.9 g (0.088 mol) of hexylamine dissolved in 80 ml of dried chloroform are dropped to the above solution at $-12°$ C. during 35 minutes. The reaction mixture is stirred at the same temperature for 1 hour and then let to stand under cooling by ice. For working up, the reaction mixture is washed 3 times with 150 ml of 5% sodium hydrogen carbonate solution each and then 3 times with 150 ml of water each. The organic phase is dried over anhydrous sodium sulfate, filtered and evaporated to give 16.4 g (71.3%) of the named product as yellow crystals after recrystallization from ethanol, m.p.: 116°–118° C.

Analysis: Calculated for $C_{16}H_{21}N_3O_2$ C 66.87; H 7.36; N 14.62%; found C 66.77; H 7.28; N 14.68%.

EXAMPLE 9

Preparation of
N-heptyl-6-methyl-4-oxo-4H-pyrido[1,2-a]pyrimidine-3-carboxamide

A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below $-10°$ C. by ice-salt. A solution of 6.5 ml (0.08 mol) of methyl chloroformate in 40 ml of chloroform is dropped to the above mixture at a temperature between $-12°$ C. and $-15°$ C. during 20 minutes. After stirring for 5 minutes, 10.14 g (0.088 mol) of heptylamine dissolved in 80 ml of chloroform are dropped to the above solution at a temperature between $-11°$ C. and $-16°$ C. during 50 minutes. The reaction mixture is stirred at the same temperature for 1 hour and then allowed to stand under cooling by ice. For working up, the reaction mixture is washed 3 times with 150 ml of 5% sodium hydrogen carbonate solution each and then 3 times with 150 ml of water each. The organic phase is dried over anhydrous sodium sulfate, filtered and evaporated to give 17.0 g (70.5%) of the named product as orange yellow crystals, m.p.: 118°–120° C.

Analysis: Calculated for $C_{17}H_{23}N_3O_2$ C 67.75; H 7.69; N 13.94%; found C 67.87; H 7.74; N 13.89%.

EXAMPLE 10

Preparation of N-octyl-6-methyl-4-oxo-4H-pyrido[1,2-a]pyrimidine-3-carboxamide

A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below $-10°$ C. by ice-salt. A solution of 6.5 ml (0.08 mol) of methyl chloroformate in 40 ml of chloroform is dropped to the above mixture at a temperature between $-13°$ C. and $-16°$ C. during 25 minutes. After stirring for 5 minutes, 11.37 g (0.088 mol) of octylamine dissolved in 80 ml of chloroform are dropped to the above solution at a temperature between $-13°$ C. and $-16°$ C. during 40 minutes. The reaction mixture is stirred at the same temperature for 1 hour and then allowed to stand overnight under cooling by ice. For working up, the reaction mixture is washed 3 times with 150 ml of 5% sodium hydrogen carbonate solution each and then 3 times with 150 ml of water each. The organic phase is dried over anhydrous sodium sulfate, filtered and evaporated to obtain 15.4 g (61.0%) of the named product as yellow crystals after recrystallization from ethanol, m.p.: 108°–110° C.

Analysis: Calculated for $C_{18}H_{25}N_3O_2$ C 68.71; H 7.99; N 13.32%; found C 68.71; H 8.08; N 13.37%.

EXAMPLE 11

Preparation of
N-tert.-octyl-6-methyl-4-oxo-4H-pyrido[1,2-a]pyrimidine-3-carboxamide A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below $-10°$ C. by ice-salt. A solution of 6.5 ml (0.08 mol) of methyl chloroformate in 40 ml chloroform is dropped to the above mixture at a temperature between $-12°$ C. and $-18°$ C. during 20 minutes. After stirring for 5 minutes, 11.37 g (0.088 mol) of tert.-octylamine dissolved in 80 ml of chloroform are dropped to the above solution at a temperature between $-18°$ C. and $-15°$ C. during 40 minutes. The reaction mixture is stirred at the same temperature for 1 hour and then allowed to stand overnight under cooling by ice. For working up, the reaction mixture is washed 3 times with 150 ml of 5% sodium hydrogen carbonate solution each, then 3 times with 150 ml of water each. The organic phase is dried over anhydrous sodium sulfate, filtered and evaporated to yield 16.1 g (63.8%) of the named product as light yellow crystals after recrystallization from ethanol, m.p.: 126°–129° C.

Analysis: Calculated for $C_{18}H_{25}N_3O_2$ C 68.54; H 7.99; N 13.32%; C 68.68; H 8.04; N 13.40%.

EXAMPLE 12

Preparation of
N-tert.-pentyl-6-methyl-4-oxo-4H-pyrido[1,2-a]pyrimidine-3-carboxamide A mixture containing 8.16 g (0.04 mol) of 6-methyl-4-oxo-4H-pyrido[1,2-a]pyrimidine-3-carboxylic acid and 6.2 ml (0.044 mol) of triethylamine in 240 ml of chloroform is cooled below $-10°$ C. by ice-salt. A solution of 4 ml (0.042 mol) of ethyl chloroformate in 20 ml of chloroform is dropped to the above mixture at a temperature between $-12°$ C. and $-17°$ C. during 15 minutes. After stirring for 5 minutes, 3.84 g (0.044 mol) of tert.-pentylamine dissolved in 40 ml of chloroform are dropped to the above solution at the same temperature during 15 minutes. The reaction mixture is stirred for 1 hour at about $-10°$ C. and then allowed to stand overnight under cooling by ice. For working up, the reaction mixture is washed 3 times with 50 ml of 5% sodium hydrogen carbonate solution each and then 3 times with 50 ml of water each. The organic phase is dried over anhydrous sodium sulfate, filtered and evaporated. The residue slowly becomes crystalline to give 5.9 g (54%) of the named compound, m.p. 87°–89° C. after recrystallization from ethanol.

Analysis: Calculated for $C_{15}H_{19}N_3O_2$ C 65.90; H 7.00; N 15.37%; found C 65.97; H 7.11; N 15.47%.

EXAMPLE 13

Preparation of
N-cyclopropyl-6-methyl-4-oxo-4H-pyrido[1,2-a]pyrimidine-3-carboxamide A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below −10° C. by ice-salt. A solution of 6.5 ml (0.08 mol) of methyl chloroformate dissolved in 40 ml of chloroform is dropped to the above mixture at a temperature between −10° C. and −17° C. during 25 minutes. After stirring for 5 minutes, 5.025 g (0.088 mol) of cyclopropylamine in 80 ml of chloroform are dropped to the above solution at the same temperature during 40 minutes. The reaction mixture is stirred for 1 hour below −10° C. and then allowed to stand overnight under cooling by ice. For working up, the reaction mixture is washed 3 times with 150 ml of 5% sodium hydrogen carbonate solution each, then 3 times with 150 ml of water each. The organic phase is dried over anhydrous sodium sulfate, filtered and evaporated to give 14.5 g (74.5%) of the named compound as light yellow crystals after recrystallization from ethanol, m.p.: 174°–176° C.

Analysis: Calculated for $C_{13}H_{13}N_3O_2$ C 64.18; H 5.38; N 17.27%; found C 64.25; H 5.42; N 17.21%.

EXAMPLE 14

Preparation of
N-cyclopentyl-6-methyl-4-oxo-4H-pyrido[1,2-a]pyrimidine-3-carboxamide A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below −10° C. by ice salt. A solution of 6.5 ml (0.08 mol) of methyl chloroformate in 40 ml of chloroform is dropped to the above mixture at −10° C. during 20 minutes. After stirring for 5 minutes, 7.49 g (0.086 mol) of cyclopentylamine dissolved in 80 ml of chloroform are dropped to the above solution at −15° C. during 30 minutes. The reaction mixture is stirred for 1 hour below −10° C., then allowed to stand overnight under cooling by ice. For working up, the reaction mixture is washed 3 times with 150 ml of 5% sodium hydrogen carbonate solution each, then 3 times with 150 ml of water each. The organic phase is dried over anhydrous sodium sulfate, filtered and evaporated to yield 14.3 g (65.9%) of the title product as yellow crystals after recrystallization from ethanol, m.p.: 158°–160° C.

Analysis: Calculated for $C_{14}H_{17}N_3O_2$ C 66.04; H 6.31; N 15.49%; found C 66.34; H 6.28; N 15.54%.

EXAMPLE 15

Preparation of
N-cyclohexyl-6-methyl-4-oxo-4H-pyrido[1,2-a]pyrimidine-3-carboxamide A mixture containing 16.32 g (0.06 mol) of 6-methyl-4-oxo-4H-pyrido[1,2-a]pyrimidine-3-carboxylic acid and 12.4 ml (0.088 mol) of triethylamine in 480 ml of chloroform is cooled below −10° C. by ice-salt. A solution of 6.5 ml (0.08 mol) of methyl chloroformate in 40 ml of chloroform is dropped to the above mixture at −10° C. during 20 minutes. After stirring for 5 minutes, 8.73 g (0.088 mol) of cyclohexylamine dissolved in 80 ml of chloroform are dropped to the above solution at −15° C. during 30 minutes. The reaction mixture is stirred for 1 hour below −10° C. and then allowed to stand overnight under cooling by ice. For working up, the reaction mixture is washed 3 times with 150 ml of 5% sodium hydrogen carbonate solution each and then 3 times with 150 ml of water each. The organic phase is dried over anhydrous sodium sulfate, filtered and evaporated to give 16.7 g (73.2%) of the named product as yellow crystals after recrystallization from ethanol, m.p.: 174°–176° C.

Analysis: Calculated for $C_{16}H_{19}N_3O_2$ C 67.35; H 6.71; N 14.72%; found C 67.29; H 6.67; N 14.78%.

EXAMPLE 16

Preparation of
N-cycloheptyl-6-methyl-4-oxo-4H-pyrido[1,2-a]pyrimidine-3-carboxamide A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below −10° C. by ice-salt. A solution of 6.5 ml (0.08 mol) of methyl chloroformate in 40 ml of chloroform is dropped to the above mixture at −10° C. during 20 minutes. After stirring for 5 minutes, 9.96 g (0.088 mol) of cycloheptylamine dissolved in 80 ml of chloroform are dropped to the above solution at a temperature between −12° C. and −15° C. during 40 minutes. The reaction mixture is stirred for 1 hour below −10° C. and then allowed to stand overnight under cooling by ice. For working up, the reaction mixture is washed 3 times with 150 ml of 5% sodium hydrogen carbonate solution each, then 3 times with 150 ml of water each. The organic phase is dried over anhydrous sodium sulfate, filtered and evaporated to obtain 20.4 g (85.2%) of the named compound as yellow crystals, m.p.: 172°–174° C.

Analysis: Calculated for $C_{17}H_{21}O_2$ C 68.20; H 7.07; N 1.03%; found C 68.27; H 7.18; N 14.10%.

EXAMPLE 17

Preparation of
N-phenyl-6-methyl-4-oxo-4H-pyrido[1,2-a]pyrimidine-3-carboxamide

A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below −10° C. by ice-salt. A solution of 6.5 ml (0.08 mol) of methyl chloroformate in 40 ml of chloroform is dropped to the above mixture at a temperature between −10° C. and −13° C. during 20 minutes. After stirring for 5 minutes, 9.19 g (0.088 mol) of aniline dissolved in 80 ml of chloroform are dropped to the above solution at a temperature between −10° C. and −13° C. during 30 minutes. The reaction mixture is stirred below −10° C. for 1 hour and then allowed to stand overnight under cooling by ice. For working up, the reaction mixture is washed 3 times with 150 ml of 5% sodium hydrogen carbonate solution each and then 3 times with 150 ml of water each. The organic phase is dried over anhydrous sodium sulfate, filtered and evaporated to give 17.6 g (78.8%) of the named compound as yellow crystals after recrystallization from ethanol, m.p.: 186°–188° C.

Analysis: Calculated for $C_{16}H_{13}N_3O_2$ C 68.81; H 4.69; N 15.04%; found C 68.87; H 4.70; N 15.10%.

EXAMPLE 18

Preparation of N-(4-fluorophenyl)-6-methyl-4-oxo-4H-pyrido[1,2-a]pyrimidine-3-carboxamide A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below $-10°$ C. by ice-salt. A solution of 6.5 ml (0.08 mol) of methyl chloroformate in 40 ml of chloroform is dropped to the above mixture at a temperature between $-12°$ C. and $-17°$ C. during 25 minutes. After stirring for 5 minutes, 9.78 g (0.088 mol) of 4-fluoroaniline dissolved in 80 ml of chloroform are dropped to the above solution at $-13°$ C. during 30 minutes. The reaction mixture is stirred below $-10°$ C. for 1 hour, then allowed to stand overnight under cooling by ice. For working up, the reaction mixture is washed 3 times with 150 ml of 5% sodium hydrogen carbonate solution each and then 3 times with 150 ml of water each. The organic phase is dried over anhydrous sodium sulfate, filtered and evaporated to give 18.3 g (77%) of the named compound as yellow crystals after recrystallization from n-propanol, m.p.: $202°-204°$ C.

Analysis: Calculated for $C_{16}H_{12}N_3O_2$ C 64.64; H 4.07; N 14.13%; found C 64.58; H 4.11; N 14.18%.

EXAMPLE 19

Preparation of N-(4-chlorophenyl)-6-methyl-4-oxo-4H-pyrido[1,2-a]pyrimidine-3-carboxamide A mixture containing 16.32 g (0.08 mol) of 6-methyl-4-oxo-4H-pyrido[1,2-a]pyrimidine-3-carboxylic acid and 12.4 ml (0.088 mol) of triethylamine in 480 ml of chloroform is cooled below $-10°$ C. by ice-salt. A solution of 6.5 ml (0.08 mol) of methyl chloroformate in 40 ml of chloroform is dropped to the above mixture at a temperature between $-10°$ C. and $-12°$ C. during 20 minutes. After stirring for 5 minutes, 11.23 g (0.088 mol) of 4-chloroaniline dissolved in 80 ml of chloroform are dropped to the above solution at $-10°$ C. during 35 minutes. The reaction mixture is stirred below $-10°$ C. for 1 hour, then allowed to stand overnight under cooling by ice. For working up, the reaction mixture is washed 3 times with 150 ml of 5% sodium hydrogen carbonate solution each and then 3 times with 150 ml of water each. The organic phase is dried over anhydrous sodium sulfate, filtered and evaporated to yield 18.5 g (73.7%) of the named compound as yellow crystals after recrystallization from ethanol, m.p.: $202°-204°$ C.

Analysis: Calculated for $C_{16}H_{12}N_3O_2$ C 61.25; H 3.85; N 13.39%; found C 61.36; H 3.90; N 13.42%.

EXAMPLE 20

Preparation of N-propyl-4-oxo-4H-pyrido[1,2-a]pyrimidine-3-carboxamide

A mixture containing 7.2 g (0.0378 mol) of 4-oxo-4H-pyrido[1,2-a]pyrimidine-3-carboxylic acid and 6.2 g (0.044 mol) of triethylamine in 240 ml of chloroform is cooled below $-10°$ C. by ice-salt. A solution of 3.25 ml (0.044 mol) of methyl chloroformate dissolved in 20 ml of chloroform is dropped to the above mixture at $-20°$ C. during 20 minutes. After stirring for 5 minutes, 2.6 g (0.04 mol) of n-propylamine dissolved in 80 ml of chloroform are dropped at $-18°$ C. during 60 minutes. The reaction mixture is stirred for 1 hour at the same temperature, then allowed to stand overnight under cooling by ice. For working up, the reaction mixture is washed 3 times with 70 ml of 5% sodium hydrogen carbonate solution each, then 3 times with 70 ml of water each. The organic phase is dried over anhydrous sodium sulfate, filtered and evaporated to yield 7.1 g (77.5%) of the named compound as light yellow crystals after recrystallization from ethanol, m.p.: $120°-122°$ C.

Analysis: Calculated for $C_{12}H_{11}N_3O_2$ C 62.87; H 4.83; N 18.33%; found C 62.81; H 4.79; N 18.39%.

EXAMPLE 21

Preparation of N-propyl-7-methyl-4-oxo-4H-pyrido-[1,2-a]pyrimidine-3-carboxamide A mixture containing 16.32 g (0.08 mol) of 7-methyl-4-oxo-4H-pyrido[1,2-a]pyrimidine-3-carboxylic acid and 12.4 ml (0.088 mol) of triethylamine in 480 ml of chloroform is cooled below $-10°$ C. by ice-salt. A solution of 6.5 ml (0.08 mol) of methyl chloroformate dissolved in 40 ml of chloroform is dropped to the above mixture at $-18°$ C. during 20 minutes. After stirring for 5 minutes, 5.2 g (0.088 mol) of propylamine dissolved in 80 ml of chloroform are dropped to the above solution at $-18°$ C. during 60 minutes. The reaction mixture is stirred at $-10°$ C. for 1 hour, then allowed to stand overnight under cooling by ice. For working up, the reaction mixture is washed 3 times with 150 ml of 5% sodium hydrogen carbonate solution each, then 3 times with 150 ml of water each. The organic phase is dried over anhydrous sodium sulfate, filtered and evaporated to obtain 17.5 g (89.2%) of the named compound as yellow crystals after recrystallization from ethanol, m.p.: $126°-128°$ C.

Analysis: Calculated for $C_{13}H_{15}N_3O_2$ C 63.66; H 6.16; N 17.13%; found C 63.69; H 6.21; N 17.18%.

EXAMPLE 22

Preparation of N-propyl-8-methyl-4-oxo-4H-pyrido[1,2-a]pyrimidine-3-carboxamide

A mixture containing 16.32 g (0.08 mol) of 8-methyl-4-oxo-4H-pyrido[1,2-a]pyrimidine-3-carboxylic acid and 12.4 ml (0.08 mol) of triethylamine in 480 ml of chloroform is cooled below $-10°$ C. by ice salt. A solution of 6.5 ml (0.08 mol) of methyl chloroformate dissolved in 40 ml of chloroform is dropped to the above mixture at $-18°$ C. during 10 minutes. After stirring for 5 minutes, 5.2 g (0.088 mol) of propylamine dissolved in 80 ml of chloroform are dropped to the above solution at $-18°$ C. during 60 minutes. The reaction mixture is stirred at $-10°$ C. for 1 hour, then allowed to stand under cooling by ice. For working up, the reaction mixture is washed 3 times with 150 mi of 5% sodium hydrogen carbonate solution each, then 3 times with 150 ml of water each. The organic phase is dried over anhydrous sodium sulfate, filtered and evaporated to give 17.3 g (88.2%) of the named compound as yellow crystals after recrystallization from ethanol, m.p.: $194°-196°$ C.

Analysis: Calculated for $C_{13}H_{15}N_3O_2$ C 63.58; H 6.16; N 17.13%; found C 63.58; H 6.21; N 17.19%.

EXAMPLE 23

Preparation of N-propyl-9-methyl-4-oxo-4H-pyrido-[1,2-a]pyrimidine-3-carboxamide A mixture containing 9.2 g (0.045 mol) of 9-methyl-4-oxo-4H-pyrido[1,2-a]pyrimidine-3-carboxylic acid and 7.05 ml (0.05 mol) of triethylamine in 280 ml of chloroform is cooled below −10° C. by ice-salt. A solution of 3.7 ml (0.045 mol) of methyl chloroformate dissolved in 25 ml of chloroform is dropped to the above mixture at −21 0° C. during 10 minutes. After stirring for 5 minutes, 2.95 g (0.05 mol) of propylamine dissolved in 50 ml of chloroform are dropped to the above solution at a temperature between −21° C. and −19° C. during 45 minutes. The reaction mixture is stirred below −10° C. for 1 hour, then allowed to stand overnight under cooling by ice. For working up, the reaction mixture is washed 3 times with 70 ml of 5% sodium hydrogen carbonate solution each, then 3 times with 70 ml of water each. The organic phase is dried over anhydrous sodium sulfate, filtered and evaporated to give 7.8 g (70.7%) of the named compound as snow-white crystals after recrystallization from ethanol, m.p.: 138°–140° C.

Analysis: Calculated for $C_{13}H_{15}N_3O_2$ C 63.66; H 6.16; N 17.13%; found C 63.69; H 6.21; N 17.18%.

EXAMPLE 24

Preparation of N-propyl-6-methyl-4-oxo-4H-pyrido[1,2-a]pyrimidine-3-acetic acid amide A mixture containing 2.18 g (0.01 mol) of 6-methyl-4-oxo-4H-pyrido[1,2-a]pyrimidine-3-acetic acid and 1.55 ml (0.011 mol) of triethylamine in 60 ml of chloroform is cooled below −10° C. by ice-salt. A solution of 0.945 g (0.01 mol) of methyl chloroformate in 5 ml of chloroform is dropped to the above mixture at −12° C. during 7 minutes. After stirring for 5 minutes, 0.65 g (0.011 mol) of propylamine dissolved in 10 ml of chloroform is dropped to the above solution at −15° C. during 10 minutes. The reaction mixture is stirred at −15° C. for 1 hour, then allowed to stand overnight under cooling by ice. For working up, the reaction mixture is washed 3 times with 40 ml of 5% sodium hydrogen carbonate solution each, then 3 times with 40 ml of water each. The organic phase is dried over anhydrous sodium sulfate, filtered and evaporated. After thoroughly triturating the residue with cold ethyl acetate, 0.8 g (30.9%) of the named compound is obtained, m.p.: 96°–98° C. after recrystallization from ethyl acetate.

Analysis: Calculated for $C_{14}H_{17}N_3O_2$ C 64.85; H 6.61; N 16.20%; found C 64.81; H 6.72; N 16.28%.

EXAMPLE 25

Preparation of N-(1-ethoxycarbonyl-2-methylpropyl)-6-methyl-4-oxo-4H-pyrido[1,2-a]pyrimidine-3-carboxamide A mixture containing 5.717 g (0.028 mol) of 6-methyl-4-oxo-4H-pyrido[1,2-a]pyrimidine-3-carboxylic acid and 4.34 ml (0.031 mol) of triethylamine in 120 ml of chloroform is cooled below −10° C. by ice-salt. A solution of 2.52 ml (0.026 mol) of methyl chloroformate in 10 ml of chloroform is dropped to the above mixture at −10° C. during 10 minutes. After stirring for 5 minutes, 3.7 g (0.028 mol) of ethyl 2-aminosobutyrate dissolved in 20 ml of chloroform are dropped to the above solution at −12° C. during 30 minutes. The reaction mixture is stirred at −10° C. for 1 hour, then allowed to stand overnight under cooling by ice. For working up, the reaction mixture is washed 3 times with 50 ml of 5% sodium hydrogen carbonate solution each, then 3 times with 50 ml of water each. The organic phase is dried over anhydrous sodium sulfate, filtered and evaporated to give 5.7 g (64.2%) of the named compound as pale yellow crystals after recrystallization from ethanol, m.p.: 136° C.

Analysis: Calculated for $C_{16}H_{19}N_3O_4$ C 60.56; H 6.03; N 13.24%; found C 60.63; H 6.13; N 13.27%.

EXAMPLE 26

Preparation of N-adamantyl-6-methyl-4-oxo-4H-pyrido[1,2-a]pyrimidine-3-carboxamide A mixture containing 4.08 (0.02 mole) of 6-methyl-4-oxo-4H-pyrido[1.2-a]pyrimidine-3-carboxylic acid and 3.1 ml (0.022 mol) of triethylamine in 120 ml of chloroform is cooled below −10° C. by ice-salt. A solution of 2.52 ml (0.026 mol) of methyl chloroformate in 10 ml of chloroform is dropped to the above mixture at −15° C. during 10 minutes. After stirring for 5 minutes, 3.33 g (0.022 mol) of 1-adamantanamine dissolved in 20 ml of chloroform are dropped to the above solution at −15 0° C. during 15 minutes. The reaction mixture is stirred below −10° C. for 1 hour, then allowed to stand overnight under cooling by ice. For working up, the reaction mixture is washed 3 times with 70 ml of 5% sodium hydrogen carbonate solution each, then 3 times with 70 ml of water each. The organic phase is dried over anhydrous sodium sulfate, filtered and evaporated to yield 4.4 g (65.2%) of the named product as pale yellow crystals after recrystallization from ethanol, m.p.: 190°–193° C.

Analysis: Calculated for $C_{20}H_{23}N_3O_2$ C 71.19; H 6.87; N 12.45%; found C 71.24; H 6.97; N 12.51%.

EXAMPLE 27

Preparation of 6-methyl-4-oxo-3-pyrrolidinocarbonyl-4H-pyrido[1,2-a]pyrimidine

A mixture containing 20.4 g (0.1 mol) of 6-methyl-4-oxo-4H-pyrido[1,2-a]pyrimidine-3-carboxylic acid and 15.5 ml (0.11 mol) of triethylamine in 600 ml of chloroform is cooled below −10° C. by ice-salt. A solution of 10 ml (0.1 mol) of methyl chloroformate dissolved in 50 ml of chloroform is dropped to the above mixture at −10° C. during 30 to 35 minutes. After stirring for 20 minutes, 9 g (0.11 mol) of pyrrolidine dissolved in 100 ml of chloroform are dropped to the above solution at a temperature between −5° C. and −8° C. during 1 hour. The reaction mixture is stirred at the same temperature for 1 hour, then allowed to stand overnight under cooling by ice. For working up, the reaction mixture is washed 3 times with 400 ml of 5% sodium hydrogen carbonate solution each, then 3 times with 400 ml of water each. The organic phase is dried over anhydrous sodium sulfate, filtered and evaporated. After suspending the oily residue in petroleum ether, 8.3 g (32.3%) of the named compound are obtained, which forms yellow crystals after recrystallization from ethanol, m.p.: 132°–134° C.

Analysis: Calculated for $C_{14}H_{15}N_3O_2$ C 65.36; H 5.88; N 16.33%; found C 65.01; H 6.04; N 16.57%.

EXAMPLE 28

Preparation of N-propyl-6-methyl-4-oxo-4H-pyrido[1,2-a]pyrimidine-3-carboxamide methanesulfonate After dissolving 1.527 g (0.00623 mol) of N-propyl-6-methyl-oxo-4H-pyrido[1,2-a]pyrimidine-3-carboxamide by heating, 0.61 ml (0.009 mol) of methanesulfonic acid is dropped to the clear yellow solution. On cooling, 1.84 g (86.8%) of the named salt are precipitated as a white crystalline substance, m.p.: 183°-185° C.

Analysis: Calculated for $C_{14}H_{18}N_3O_5S$ C 49.40; H 5.33; N 12.34%; found C 49.31; H 5.25; N 12.38%.

EXAMPLE 29

Preparation of N-propyl-6-methyl-4-oxo-4H-pyrido[1,2-a]pyrimidine-3-carboxamide hydrochloride After dissolving 10 g (0.041 mol) of N-propyl-6-methyl-4-oxo-4H-pyrido[1,2-a]pyrimidine-3-carboxamide in 150 ml of ethanol by heating, 10 ml of ethanol containing 20% hydrogen chloride are dropped to the clear yellow solution (PH=1). After cooling, the precipitated crystals are filtered to give 9.3 g (81.0%) of the named salt, m.p.: 206°-208° C.

Analysis: Calculated for $C_{13}H_{16}ClN_3O_2$ C 55.42; H 5.72; N 14.91%; found C 55.47; H 5.81; N 14.87%.

EXAMPLE 30

Preparation of N-cyclopentyl-6-methyl-4-oxo-4H-pyrido[1,2-a]pyrimidine-3-carboxamide hydrochloride After dissolving 3 g (0.011 mol) of N-cyclopentyl-6-methyl-4-oxo-4H-pyrido[1,2-a]pyrimidine-3-carboxamide in 45 mi of ethanol by heating, 10 ml of ethanol containing 20% hydrogen chloride ar2 added to the clear yellow solution (pH=1). After cooling, the precipitated crystals are filtered to obtain 2.5 g (75.53%) of the named salt, m.p.: 205°-209° C.

Analysis: Calculated for $C_{15}H_{18}ClN_3O_2$ C 56.54; H 5.89; N 13.65%; found C 58.27; H 6.11; N 13.69%.

EXAMPLE 31

Preparation o N-cyclopentyl-7-methyl-4-oxo-4H-pyrido[1,2-a]pyrimidine-3-carboxamide A mixture containing 1.22 g (0.006 mol) of 7-methyl-4-oxo-4H-pyrido[1,2-a]pyrimidine-3-carboxylic acid and 0.84 ml (0.006 mol) of triethylamine in 40 ml of chloroform is cooled below −10° C. by ice-salt. A solution of 0.46 ml (0.006 mol) of methyl chloroform, ,ate in 3 ml of chloroform is dropped to the above mixture at −18° C. during 10 minutes. After stirring for 5 minutes, 0.56 g (0.0066 mol) of cyclopentylamine dissolved in 6 ml of chloroform is dropped to the above solution which is then stirred at −10° C. for 1 hour and allowed to stand overnight under cooling by ice. For working up, the reaction mixture is washed 3 times with 15 ml of 5% sodium hydrogen carbonate solution each, then 3 times with 15 ml of water each. The organic phase is dried over anhydrous sodium sulfate, filtered and evaporated to give 0.8 g (49.2%) of the named compound as white crystals after recrystallization from ethanol, m.p.: 162°-164° C.

Analysis: Calculated for $C_{15}H_{17}N_3O_2$ C 66.04; H 6.31; N 15.49%; found C 66.19; H 6.57; N 15.42%.

EXAMPLE 32

Preparation of N-cyclopentyl-B-methyl-4-oxo-4H-pyrido[1,2-a]pyrimidine-3-carboxamide A mixture containing 1.22 g (0.006 mol) of 8-methyl-4-oxo-4H-pyrido[1,2-a]pyrimidine-3-carboxylic acid and 0.84 ml (0.006 mol) of triethylamine in 40 ml of chloroform is cooled below −10° C. by ice-salt. A solution of 0.46 ml (0.006 mol) of methyl chloroformate in 3 ml of chloroform is dropped to the above mixture at −15° C. during 10 minutes. After stirring for 5 minutes, 0.56 g (0.0066 mol) of cyclopentylamine dissolved in 6 ml of chloroform is dropped to the above solution. The reaction mixture is stirred at −10° C. for 1 hour, then allowed to stand overnight under cooling by ice. For working up, the reaction mixture is washed 3 times with 15 ml of 5% sodium hydrogen carbonate solution each, then 3 times with 15 ml of water each. The organic phase is dried over anhydrous sodium sulfate, filtered and evaporated to yield 0.9 g (55%) of the named compound as a crystalline substance after recrystallization from ethanol, m.p.: 220°-222° C.

Analysis: Calculated for $C_{15}H_{17}N_3O_2$ C 66.04; H 6.31; N 15.49%. found C 66.11; H 6.38; N 15.41%.

EXAMPLE 33

Preparation of N-cyclopentyl-9-methyl-4-oxo-4H-pyrido[1,2-a]pyrimidine-3-carboxamide A mixture containing 1.22 g (0.006 mol) of 9-methyl-4-oxo-4H-pyrido[1,2-a]pyrimidine-3-carboxylic acid and 0.84 ml (0.006 mol) of triethylamine in 40 ml of chloroform is cooled below −10° C. by ice-salt. A solution of 0.46 ml (0.006 mol) of methyl chloroformate in 3 ml of chloroform is dropped to the above mixture at −15° C. during 10 minutes. After stirring for 5 minutes, 0.56 g (0.0066 mol) of cyclopentylamine dissolved in 6 ml of chloroform is dropped to the above reaction mixture which is then stirred at −10° C. for 1 hour and then allowed to stand overnight under cooling by ice. For working up, the reaction mixture is washed 3 times with 15 ml of 5% sodium hydrogen carbonate solution each, then 3 times with 15 ml of water each. The organic phase is dried over anhydrous sodium sulfate, filtered and evaporated to yield 0.6 g (36.9%) of the named compound as a white crystalline substance after recrystallization from ethanol, m.p.: 170°-171° C.

Analysis: Calculated for $C_{15}H_{17}N_3O_2$ C 66.04; H 6.31; N 15.49%; found C 65.94; H 6.27; N 15.53%.

We claim:

1. A compound of the Formula (I)

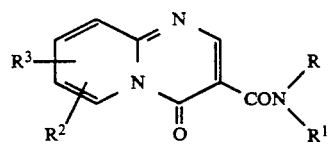

(I)

wherein

R is a $C_1$ to $C_{12}$ alkyl group substituted by $C_1$ to $C_4$ alkoxycarbonyl, a $C_3$ to $C_9$ cycloalkyl group, an adamantyl group, or a phenyl group substituted by halogen, $C_1$ to $C_4$ alkyl, $C_2$ to $C_5$ alkoxy, hydroxy, trifluoromethyl, cyano, $C_1$ to $C_4$ alkoxycarbonyl, carboxy or methylenedioxy;

$R^1$ is hydrogen or a $C_1$ to $C_4$ alkyl group; or R and $R^1$ together form a —$(CH_2)_n$— chain, wherein n is 4,5 or 6;

$R^2$ is hydrogen, a $C_1$ to $C_4$ alkyl group or halogen; and $R^3$ is hydrogen or a $C_1$ to $C_4$ alkyl group;

or a pharmaceutically acceptable acid addition salt thereof.

2. A compound of the Formula (IA)

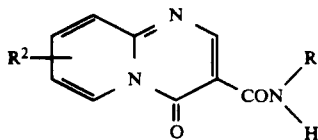

wherein
R is $C_3$ to $C_9$ cycloalkyl; and
$R^2$ is $C_1$ to $C_4$ alkyl; or a pharmaceutically acceptable acid addition salt thereof.

3. The compound of the Formula (I) defined in claim 2 which is N-cyclopentyl-6-methyl-4-oxo-4H-pyrido(1,2-a)pyrimidine-3-carboxamide or a pharmaceutically acceptable acid addition salt thereof.

4. The compound of the Formula (I) defined in claim 2 which is N-cyclopentyl-9-methyl-4-oxo-4H-pyrido(1,2-a)-pyrimidine-3-carboxamide or a pharmaceutically acceptable acid addition salt thereof.

5. The compound of the Formula (I) defined in claim 2 wherein R is a $C_3$ to $C_9$ cycloalkyl group or a pharmaceutically acceptable acid addition salt thereof.

6. The compound of Formula (I) defined in claim 2 wherein R is a cyclopentyl group or a pharmaceutically acceptable acid addition salt thereof.

7. An anti-ulcer pharmaceutical composition which comprises as active ingredient a therapeutically effective amount of the compound of the Formula (I) defined in claim 1 or a pharmaceutically acceptable acid addition salt thereof in admixture with a pharmaceutically acceptable inert carrier.

* * * * *